(12) United States Patent
Sugiyama et al.

(10) Patent No.: US 10,863,913 B2
(45) Date of Patent: Dec. 15, 2020

(54) BIOINFORMATION MEASUREMENT DEVICE

(71) Applicant: TS TECH CO., LTD., Saitama (JP)

(72) Inventors: Shinji Sugiyama, Tochigi (JP); Takayuki Inose, Tochigi (JP)

(73) Assignee: TS TECH CO., LTD., Saitama (JP)

( * ) Notice: Subject to any disclaimer, the term of this patent is extended or adjusted under 35 U.S.C. 154(b) by 109 days.

(21) Appl. No.: 16/075,194

(22) PCT Filed: Jan. 31, 2017

(86) PCT No.: PCT/JP2017/003469
§ 371 (c)(1),
(2) Date: Aug. 3, 2018

(87) PCT Pub. No.: WO2017/135263
PCT Pub. Date: Aug. 10, 2017

(65) Prior Publication Data
US 2019/0038231 A1    Feb. 7, 2019

(30) Foreign Application Priority Data

Feb. 5, 2016  (JP) .................................. 2016-021003
Oct. 14, 2016 (JP) .................................. 2016-202932

(51) Int. Cl.
*A61B 5/0408*    (2006.01)
*A61B 5/00*      (2006.01)
(Continued)

(52) U.S. Cl.
CPC ............ *A61B 5/0408* (2013.01); *A61B 5/024* (2013.01); *A61B 5/02444* (2013.01);
(Continued)

(58) Field of Classification Search
CPC .. A61B 5/0408; A61B 5/04085; A61B 5/6893
See application file for complete search history.

(56) References Cited

U.S. PATENT DOCUMENTS

| 7,684,854 B2 * | 3/2010 | Park ..................... A61B 5/0428 |
|---|---|---|
| | | 600/382 |
| 2014/0213882 A1 * | 7/2014 | Chung ................. A61B 5/0408 |
| | | 600/395 |

(Continued)

FOREIGN PATENT DOCUMENTS

| JP | 2009-50679 A | 3/2009 |
|---|---|---|
| JP | 2013-220322 A | 10/2013 |

(Continued)

OTHER PUBLICATIONS

International Search Report dated Apr. 25, 2017 for corresponding International Application No. PCT/JP2017/003469. With English Translation.

(Continued)

*Primary Examiner* — Lee S Cohen
(74) *Attorney, Agent, or Firm* — Michael Best & Friedrich LLP

(57) ABSTRACT

Bioinformation of a seated person is more accurately measured. A heartbeat measurement device for measuring heartbeat of a person seated on a vehicle seat has heartbeat sensors and a circuit substrate: the heartbeat sensors have leading wires which output electric signals corresponding to a heartbeat and constitute a transmission path for the electric signals; and the circuit substrate has input terminals which receives the electric signals output from the heartbeat sensors, and a differential amplifier which amplifies the electric signals input to the input terminals. The heartbeat sensors and the circuit substrate are disposed in positions adjacent to each other in the vehicle seat, and terminal portions of the leading wires come out from portions adjacent to the circuit board of the heartbeat sensors are connected to the input terminals in a state abutting the input terminals.

16 Claims, 9 Drawing Sheets

(51) Int. Cl.
*B60N 2/00* (2006.01)
*A61B 5/024* (2006.01)
*A61B 5/18* (2006.01)
*B60R 16/023* (2006.01)

(52) U.S. Cl.
CPC ............ *A61B 5/04085* (2013.01); *A61B 5/18* (2013.01); *A61B 5/6893* (2013.01); *B60N 2/002* (2013.01); *B60R 16/023* (2013.01)

(56) References Cited

U.S. PATENT DOCUMENTS

2014/0323838 A1\* 10/2014 Nishii .................. A61B 5/6891
 600/382
2015/0133804 A1   5/2015  Sugiyama et al.
2016/0089084 A1   3/2016  Sugiyama
2019/0038231 A1   2/2019  Sugiyama et al.

FOREIGN PATENT DOCUMENTS

| JP | 2014-212971 A | 11/2014 |
| JP | 2017-140358 A | 8/2017 |
| WO | 2014/185532 A1 | 11/2014 |
| WO | WO2014185532 | \* 11/2014 |

OTHER PUBLICATIONS

Japanese Office Action dated Feb. 25, 2020 for the corresponding Japanese patent application No. 2019-017372, with machine English translation.

\* cited by examiner

SEAT WIDTH DIRECTION

SEAT WIDTH DIRECTION

BIOINFORMATION MEASUREMENT DEVICE

CROSS-REFERENCE TO RELATED APPLICATIONS

This application is entering into the national phase of PCT Application Number PCT/JP2017/003469, filed on Jan. 31, 2017, which claims the benefit of priority from the Japanese Patent Application Number 2016-021003, filed on Feb. 5, 2016, and Japanese Patent Application Number 2016-202932, filed on Oct. 14, 2016, the entire contents of which are incorporated herein by reference.

TECHNICAL FIELD

The present invention relates to a bioinformation measurement device, and particularly directed to a bioinformation measurement device for measuring a bioinformation of a seated person who is seated on a seat.

BACKGROUND ART

Among devices which measure a bioinformation, there are devices which measure a bioinformation of a seated person who is seated on a seat. An example of such devices is a device which measures a heartbeat of a seated person of a vehicle seat (see the Patent Literature 1). The measurement device described in the Patent Literature 1 measures a heartbeat of a seated person by using an electrostatic capacitive coupling type sensor which detects a body potential of a seated person.

More specifically, in the measurement device described in the Patent Literature 1, the electrostatic capacitive coupling type sensor detects a body potential of a seated person and outputs an electric signal according to the detected potential. The output signal from the sensor is finally received by an arithmetic device, after subjected to an amplification processing, a filter processing, etc. By analyzing a waveform etc. of the received electric signal, the arithmetic device calculates a heartbeat (strictly, a heart rate) of the seated person from the electric signal.

CITATION LIST

Patent Literature

PATENT LITERATURE 1: JP2013-220322

SUMMARY OF INVENTION

Technical Problem

Incidentally, in the measurement device described in the Patent Document 1, a circuit for amplifying the output signal from the sensor is interposed between the sensor and the arithmetic device. However, the more the sensor is separated from the amplification processing circuit, the longer a route for transmitting an electric signal output from the sensor (a transmission path) becomes. The longer the transmission path becomes, the more easily a noise is superposed on the output signal from the sensor. If a noise is superposed on an output signal from a sensor in this way, it is concerned that a heartbeat measurement based on the signal is affected by the noise.

As for a substrate constituting the circuit (a circuit substrate), it is desirable that the substrate is disposed in a position where a size or a quality (for example, riding comfort) of a seat is hardly affected thereby.

Thus, the present invention has been achieved in light of the problem, and an object thereof is to provide a bioinformation measurement device capable of measuring a bioinformation of a seated person more accurately.

In addition, another object of the present invention is to dispose a circuit substrate in a position where a size or a quality of a seat is hardly affected thereby.

Solution to Problem

According to the bioinformation measurement device of the present invention, the problem is solved by a bioinformation measurement device for measuring a bioinformation of a seated person who is seated on a seat, which is provided with: a sensor which outputs an electric signal according to a bioinformation, with a leading wire constituting a transmission path for the electric signal; and a circuit substrate having an input terminal provided to receive the electric signal from the sensor, and an amplification unit which amplifies the electric signal input to the input terminal, wherein the sensor and the circuit substrate are disposed in positions adjacent to each other in the seat; and in the sensor, a terminal portion of the leading wire come out from a portion adjacent to the circuit substrate is connected to the input terminal in a state abutting the input terminal.

In the bioinformation measurement device of the present invention configured as above, the sensor and the circuit substrate are disposed in positions adjacent to each other. In the sensor, a terminal portion of the leading wire, which is come out from a portion adjacent to the circuit substrate, is directly connected to the input terminal of the circuit substrate. This allows configuring a route (a transmission path), through which an output signal from the sensor is transmitted, as short as possible. As a result, it is unlikely to generate the superposition of the output signal from the sensor and the noise, which is caused by the long transmission path, and thus, it becomes possible to effectively control an influence of the noise.

In the above described configuration, it is also preferred that the circuit substrate is attached to the seat so as to be positioned in the width direction center of the seat.

In the above described configuration, a circuit substrate is attached to the seat so as to be positioned in the width direction center of the seat. On the other hand, the width direction center of the seat is a position which faces a center of the body (a median line) of a seated person while the seated person is seated on the seat. By utilizing such positional relationship, it becomes possible to easily dispose a circuit substrate to a position where a quality of a seat is hardly affected thereby.

It is also preferred that the above described structure has a plural number of the sensors, and the plural number of the sensors are disposed in a state arranged across a gap in the width direction of the seat, and the circuit substrate is disposed within the gap, in a state sandwiched between the sensors.

In the above described structure, the circuit substrate is disposed between the sensors arranged in the width direction of the seat. Disposing the circuit substrate by utilizing the gap between the sensors in this manner, it becomes possible to control upsizing of a seat due to attachment of the circuit substrate.

It is also preferred that; the above described structure is provided with a guard ring disposed in a manner surrounding the sensor; the sensor is disposed along a face abutting a seated person of the seat; and the sensor, the guard ring, and the circuit substrate are disposed in a state arranged along the width direction of the seat.

In the above described configuration, since the sensor, the guard ring, and the circuit substrate are disposed in a horizontal arrangement, it becomes possible to make more compact space for installing each of the equipment, as compared with a structure in which each of the above described equipment is disposed off from each other.

In the above described structure, it is also preferred that the circuit substrate is attached so as to be positioned in the width direction center of a seatback provided to the seat.

In the above described structure, the circuit substrate is positioned in the width direction center of the seatback. Thus, when the back of a seated person leans on the seatback, the circuit substrate is located in the same position as a site positioned between the right and left pair of erector spinae of the back of the seated person, in the seat width direction. This makes it hard for the circuit substrate to touch the back (specifically, a site corresponding to the right and left pair of erector spinae) of the seated person.

In the above described structure, it is also preferred that the circuit substrate is attached so as to be positioned in the width direction center of a seat cushion provided to the seat.

In the above described structure, the circuit substrate is positioned in the width direction center of the seat cushion. Therefore, when the buttocks of a seated person are put on the seat cushion, the circuit substrate is located in the same position as a site corresponding to the gluteal cleft portion of the buttocks of the seated person, in the seat width direction. This makes it hard for the circuit substrate to touch the buttocks of the seated person.

In the above described structure, it is also preferred that the sensor and the circuit substrate are attached to each of the seat cushion and the seatback provided to the seat, and a range in which the circuit substrate attached to the seat cushion is located in the seat width direction and a range in which the circuit substrate attached to the seatback is located in the width direction overlap with each other.

In the above described structure, location ranges in the seat width direction of the circuit substrate attached to the seat cushion and the circuit substrate attached to the seatback are in substantially a same position in the seat width direction. In this manner, it becomes possible to attach the circuit substrate to each of the seat cushion and the seatback, so as to be properly settled thereon. This allows an attachment work of the circuit substrate to be performed comparatively easily.

Effects of Invention

According to the present invention, it becomes possible to configure the route for transmitting an output signal from the sensor as short as possible, to effectively control a situation that a noise is easily superposed on an output signal from the sensor.

According to the present invention, it becomes also possible to easily dispose a circuit substrate to a position where a quality of a seat is hardly affected thereby.

According to the present invention, it becomes also possible to control upsizing of a seat due to attachment of a circuit substrate.

According to the present invention, it becomes also possible to make more compact space for installing each of the sensor, the guard ring, and the circuit substrate.

In addition, according to the present invention, the circuit substrate is located in the same position as a site positioned between the right and left pair of erector spinae of the back of a seated person in the seat width direction, when the back of the seated person leans on the seatback, since the circuit substrate is disposed in the width direction center of the seatback. As a result, it becomes hard for the circuit substrate to touch the back of a seated person.

In addition, according to the present invention, when the buttocks of a seated person are put on a seat cushion, the circuit substrate is located in the same position as a site corresponding to the gluteal cleft portion of the buttocks of the seated person, in the seat width direction, since the circuit substrate is disposed in the width direction center of the seat cushion. As a result, it becomes hard for the circuit substrate to touch the buttocks of a seated person.

According to the present invention, it becomes also possible to attach the circuit substrate to each of the seat cushion and the seatback, so as to be properly settled thereon.

DESCRIPTION OF EMBODIMENTS

Hereinbelow, an embodiment of the present invention (the present embodiment) is described. Incidentally, in the following, a seat mounted on a vehicle (hereinbelow, a vehicle seat) is described as a specific example of a seat. However, the present invention can also be applied to a seat other than vehicle seats. For example, the present invention can also be applied to a seat to be mounted on a conveyance other than vehicles, or a seat to be used in a building such as a house or a facility.

In the following description, "seat width direction" corresponds to the width direction of the seat, more particularly, corresponds to the lateral width direction (right to left direction) of a vehicle seat. "Front to back direction" corresponds to the front to back direction of the seat, and coincides with a traveling direction of the vehicle on which the vehicle seat is mounted. "Height direction" corresponds to the vertical direction of the seat, particularly, the height direction of the vehicle seat in a state capable of seating, and more particularly, the direction from the lower end toward the upper end of a seatback of the vehicle seat. Incidentally, in the following description, contents concerning a position, an orientation, or the like of each of equipment are contents in a state that the equipment is attached to the vehicle seat.

Outline of Bioinformation Measurement Device According to Present Embodiment

First, outline of the bioinformation measurement device according to the present embodiment is described. The bioinformation measurement device according to the present embodiment is a heartbeat measurement device 1 that measures a heartbeat of a seated person as a bioinformation of the seated person seated on a vehicle seat. More particularly, while a seated person is seated on the vehicle seat, the heartbeat measurement device 1 detects a body potential of the seated person with an electrostatic capacitive coupling type sensor attached to the vehicle seat. Then, the heartbeat measurement device 1 measures a heartbeat of the seated person on the basis of an electric signal output by the sensor according to the body potential of the seated person.

Figure 1:
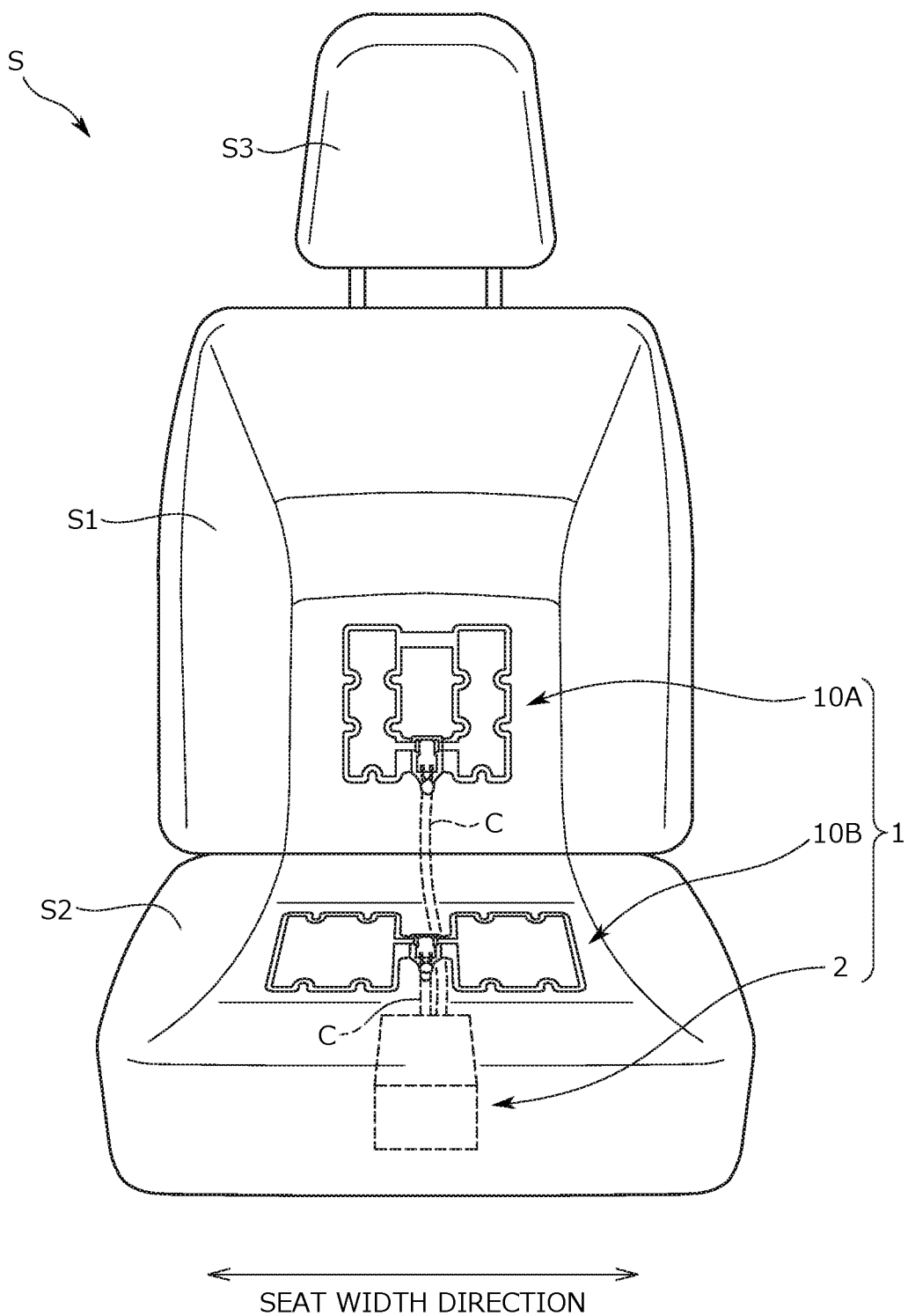
FIG. 1 is a view showing a vehicle seat to which a bioinformation measurement device according to an embodiment of the present invention is attached.

A structure of the heartbeat measurement device 1 is outlined with referring to FIG. 1. FIG. 1 is a front view of a vehicle seat S to which the heartbeat measurement device 1 is attached. Incidentally, the vehicle seat S has a structure substantially identical to that of a publicly known vehicle seat, except for a point that the heartbeat measurement device 1 is attached thereto. That is, the vehicle seat S according to the present embodiment is provided with a seatback S1 against which the back of a seated person leans, a seat cushion S2 that supports the buttocks of a seated person from below, and a headrest S3 that supports the head of a seated person. The seatback S1 and the seat cushion S2 are each configured by placing a pad material in a frame which constitutes a skeleton of the seatback S1 or the seat cushion S2, and covering surface of the pad material with a skin material.

The heartbeat measurement device 1 has sensor units 10A and 10B as illustrated in FIG. 1, and an ECU (Electric Control Unit) 2 as an arithmetic device, as main constituent elements. One sensor unit 10A and one sensor unit 10B are respectively attached to the seatback S1 and the seat cushion S2, as shown in FIG. 1. More particularly, one sensor unit 10A is attached to a portion of the seatback S1, which is a portion faced to the back of a seated person when the seated person is seated on the vehicle seat S. The other sensor unit 10B is attached to a portion of the seat cushion S2, which is a portion faced to the buttocks of a seated person when the seated person is seated on the vehicle seat S.

Each of the sensor units 10A and 10B has an electrostatic capacitive coupling type sensor (specifically, a heartbeat sensor 11 which will be described later) which electrostatic-capacitively coupled to the body of a seated person to detect a body potential of the seated person. Then, each of the sensor units 10A and 10B outputs an electric signal according to the body potential of the seated person detected by the sensor to ECU2.

Incidentally, in the structure illustrated in FIG. 1, each of the sensor units 10A and 10B are respectively adhered to each surface (strictly, the face to come in contact with the body of a seated person) of the seatback S1 and the seat cushion S2, with being exposed. In such a structure, the electrostatic capacitive coupling type sensor provided to each of the sensor units 10A and 10B is to be electrostatic-capacitively coupled the body of a seated person through a cloth of the seated person. However, this is not a limitation, and the sensor units 10A, 10B may be provided in a state sandwiched between the skin material and the pad material in each of the seatback S1 and the seat cushion S2. In such a case, each of the sensor units 10A and 10B is electrostatic-capacitively coupled the body of a seated person through the skin material and a cloth of the seated person.

The ECU2 receives an electric signal output from each of the sensor units 10A and 10B, and analyzes the electric signal, to calculate a heart rate of a seated person. In this connection, although explanation of specific method of calculating the heart rate based on output signals from the sensor units 10A and 10B is omitted, a publicly known calculation method (for example, the calculation method described in JP No. 2015-123359) is available.

In the ECU2, when an output signal from the sensor unit 10A or 10B is analyzed, the output signal is subjected to an amplification processing, a filter processing, or the like. That is, circuits for carrying out each of the processing described above are incorporated in the ECU2, and a corresponding signal processing is performed in each of the circuits. In other words, in the present embodiment, the ECU2 has a function as an instrumentation amplifier, to further amplify an electric signal which has been amplified by a differential amplifier 30 described later, and to subject the signal after amplified to a filter processing by using a high pass filter or a low pass filter.

In the present embodiment, the ECU2 is disposed in the backside (a lower side) of the seat cushion S2, as shown in FIG. 1. As shown in the same figure, between each of the sensor units 10A or 10B and the ECU2, cables C for linking the two are laid. One end of each of the cables C is joined into the ECU2, and the other end is connected to each sensor unit 10A or 10B. Incidentally, the cables C are laid so as to go around from the front side (the exposed side) to the backside of the vehicle seat S, penetrating the skin material and the pad material which constitute the seatback S1 and the seat cushion S2, and as shown in FIG. 1.

Detailed Structure of Sensor Unit

Figure 2:
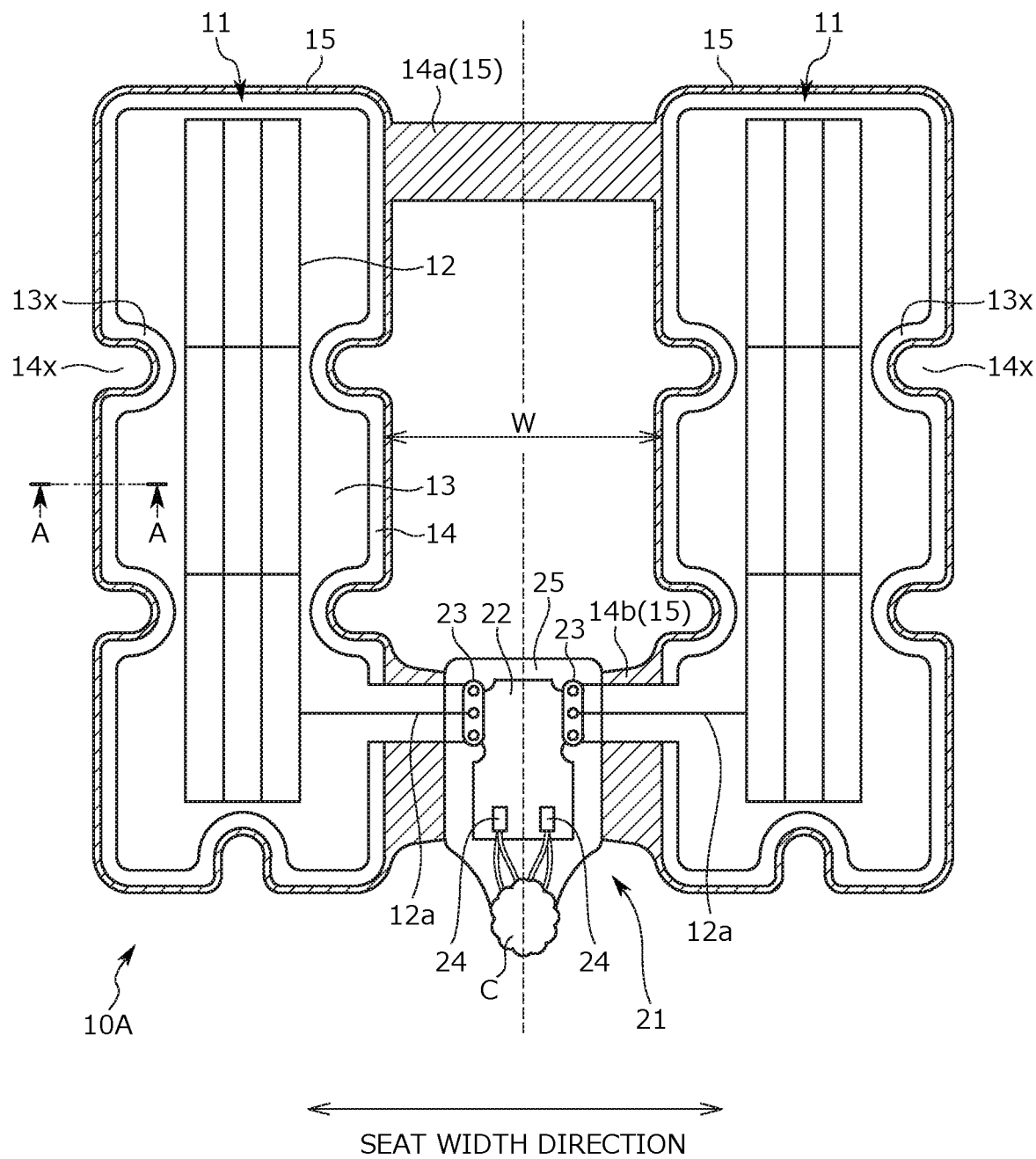
FIG. 2 is a front view of a sensor and a circuit substrate attached to a seatback.

Next, detailed structures of the sensor units 10A and 10B are described. First, the sensor unit 10A attached to the seatback S1 is described with referring to FIG. 2. FIG. 2 is a view of a sensor unit 10A attached to a seat back S1, as viewed from the front (ahead) of the vehicle seat S.

As shown in FIG. 2, the sensor unit 10A has a right and left pair of heartbeat sensors 11, a buffer circuit unit 21, and a base film 14 on which the heartbeat sensors 11 and the buffer circuit unit 21 are placed. In addition, a guard ring 15 is formed on the base film 14. Hereinbelow, each portion of the sensor unit 10A is described in detail.

(Heartbeat Sensor 11)

The heart beat sensor 11 is an electrostatic capacitive coupling type sensor which is disposed on the front face (the contact face with a seated person) of the seatback S1 via the base film 14. The heartbeat sensor 11 detects a body potential of a seated person when the back of the seated person leans against the seatback S1, and outputs an electric signal according to the detected result. Here, a body potential of a seated person generally changes according to a heartbeat (a heart rate) of the seated person, which means that the heartbeat sensor 11 outputs an electric signal according to a heartbeat of a seated person.

Incidentally, in the present embodiment, the heartbeat sensor 11 is installed in plural numbers, specifically, disposed in a right and left pair (i.e., two), symmetrically, with having the center position of the seatback S1 in the seat width direction as a boundary. This is because, a potential difference (a potential difference signal) between electric signals individually output from the right and left pair of heartbeat sensors 11 is required in measuring a heartbeat of a seated person.

Incidentally, the right and left pair of heartbeat sensors 11 is attached to the seatback S1, so as to be arranged across a predetermined gap in the seat width direction. In this manner, when the back of a seated person leans on the seat back S1, the right and left pair of heartbeat sensors 11 is located in positions across the heart of the seated person in the seat width direction.

In this connection, a width of the above described gap (a length in the seat width direction, which is represented by w in FIG. 2) is preferably configured to be 80-150 mm. If the gap is configured to be in the above described range, when the back of a seated person leans against the seatback S1, each of the heartbeat sensors 11 faces to a site corresponding to the erector spinae of the back of the seated person, making it easy to contact with the site (i.e., the electrostatic coupling is facilitated).

A structure of the heartbeat sensor 11 is described. Each of the heartbeat sensors 11 is formed of a sheet-shaped electrode, and has a substantially rectangular external configuration, as shown in FIG. 1. Each of the heartbeat sensors 11 has an area and a capacitance sufficient to detect a body potential of a seated person.

Figure 3:
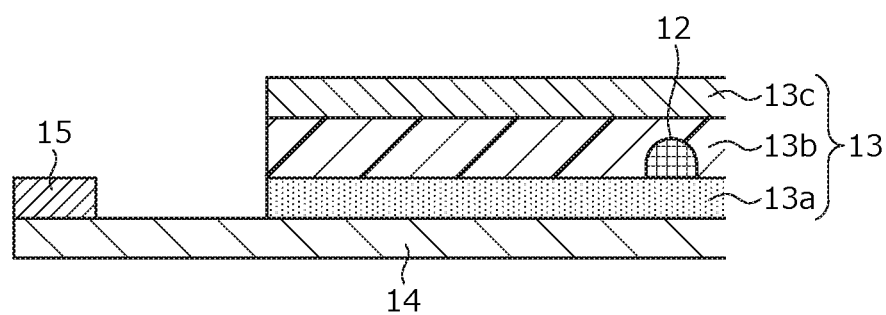
FIG. 3 is a cross-sectional view of a sensor, and is a schematic view showing the A-A cross section in FIG. 2.

The structure of the heartbeat sensor 11 is described more in detail. Each of the heartbeat sensors 11 is formed of a leading wire 12 and a base unit 13 that encloses the leading wire 12. The base unit 13 is formed of a substantially rectangular sheet and defines the outer shape of the heartbeat sensor 11. In the present embodiment, the base unit 13 has a laminated structure as shown in FIG. 3. FIG. 3 is a cross-sectional view of a heartbeat sensor 11, which is a schematic view showing the A-A cross section in FIG. 2.

As shown in FIG. 3, the base unit 13 has a lowermost layer 13a, an intermediate layer 13b, and an uppermost layer 13c. The lowermost layer 13a is a resin film made of PET (Poly Ethylene Terephthalate). The intermediate layer 13b is a resin film made of a carbon resin. The uppermost layer 13c is a coating film of a metal ink including barium titanate.

As shown in FIG. 3, the leading wire 12 is disposed between the lowermost layer 13a and the intermediate layer 13b. The leading wire 12 is made of silver, and forms a transmission path for electric signals generated by the heartbeat sensor 11 according to a body potential of a seated person. That is to say, an electric signal is transmitted through the leading wire 12 in the heartbeat sensor 11, and finally output to the outside of the heartbeat sensor 11, through the terminal portion 12a of the leading wire 12.

Incidentally, as shown in FIG. 2 the leading wires 12 are wired in a lattice shape in the base unit 13. That is, in the base unit 13, the leading wires 12 are wired correspondingly to the external configuration. Specifically, the leading wires 12 is present in plural numbers in such a state that leading wires 12 disposed along the longitudinal direction of the base portion 13 and leading wires 12 disposed along the short side direction of the base portion 13 intersect each other.

A portion corresponding to the terminal portion 12a of the leading wire 12 (in other words, a portion positioned in the most downstream side of the transmission path of the electric signal) is wired in a manner deviating from the other portions. Describing specifically with referring to FIG. 2, a portion of the base unit 13 including the terminal portion 12a of the leading wire 12 protrudes from the other portion (substantially the rectangular portion), inward in the seat width direction. This protruding portion extends toward the buffer circuit unit 21, together with the terminal portion 12a of the leading wire 12. Then, the terminal portion 12a of the leading wire 12 is joined into a circuit substrate 22 provided in the buffer circuit unit 21, more strictly, to an input terminal 23 of the circuit substrate 22.

As for the external configuration of the heartbeat sensor 11, arcuate notches 13x are formed in an outer edge portion of the heartbeat sensor 11 (strictly, the base unit 13), as shown in FIG. 2. Specifically, each two notches 13x are formed on one end portion and the other end portion in the short side direction of the outer edge portion of the base unit 13. Additionally, one notch 13x is formed on one end portion in the longitudinal direction of the outer edge portion of the base unit 13. By forming the notches 13x in this manner in several portions of the outer edge portion of the base unit 13, it becomes possible to alleviate influence to the heartbeat sensor 11, when the back of a seated person leans against the seatback S1.

Specifically, when the back of a seated person leans against the seatback S1, a load from the back of the seated person acts on the heartbeat sensor 11. Due to this load, the base unit 13 in the heartbeat sensor 11 is bent, and at this time, if a wrinkle is generated, the leading wire 12 is curved along the wrinkle. Then, a stress is concentrated to the curved portion, causing a concern that the leading wire 12 is disconnected. In contrast, in the present embodiment, since the notches 13x are formed in the outer edge portion of the base unit 13, when the base unit 13 is bent, the bending is not accompanied by a wrinkle. In this manner, it becomes possible to effectively control the bending of the leading wire 12, and a disconnection caused thereby.

(Base Film 14)

The base film 14 is a substrate for attaching the right and left pair of heartbeat sensors 11 to the front face (the backrest face) of the seatback S1. In the present embodiment, the base film 14 is formed of an acrylic film, and has a substantially square external configuration. The heartbeat sensor 11 is adhered to the front face of the base film 14, and the back face of the base film 14 is attached to a predetermined position in the front face of the seatback S1.

As shown in FIG. 2, the base film 14 has an area sufficient to place the right and left pair of heartbeat sensors 11. That is, in the present embodiment, two heartbeat sensors 11 are placed on a single base film 14. For this, number of parts is reduced, as compared with a structure in which the base film 14 is provided individually to heartbeat sensors 11. However, this is not a limitation, and the structure may also be such that the base film 14 is separately provided individually to the heartbeat sensors 11.

In the base film 14, the portion positioned between the heartbeat sensors 11 is punched out in a substantially rectangular shape as shown in FIG. 2. In the upper side and the lower side of this punched out portion, linking units 14a and 14b that link between the heartbeat sensors 11 are formed. By linking the heartbeat sensors 11 with these linking units 14a and 14b, it becomes possible to handle the right and left pair of heartbeat sensors 11 integrally. For example, in an attachment work of the heartbeat sensors 11, it is possible to attach the right and left pair of heartbeat sensors 11 integrally. However, this is not a limitation, and the structure may also be such that the right and left pair of heartbeat sensors 11 is separated, without being linked.

As shown in FIG. 2, arcuate notches 14x are formed similarly in an edge portion of the base film 14, in portions adjacent to the notches 13x formed on the base unit 13 of the heartbeat sensor 11. In this manner, the base film 14 also bends without generating a wrinkle, when the back of a seated person leans against the seatback S1. As a result, it becomes possible to more effectively control a bending of the leading wire 12 which accompanies generation of a wrinkle, and a disconnection caused thereby.

(Buffer Circuit Unit 21)

The buffer circuit unit 21 relays data between the heartbeat sensor 11 and the ECU2. This buffer circuit unit 21 amplifies an output signal (an electric signal) from each of the heartbeat sensors 11, and outputs the amplified signal towards the ECU2. The buffer circuit unit 21 is disposed between the heartbeat sensors 11 in the seat width direction. More particularly, the buffer circuit unit 21 is placed on the lower side linking unit 14b in the base film 14.

A structure of the buffer circuit unit 21 is described. The buffer circuit unit 21 is provided with a circuit substrate 22, an input terminal 23, and an output terminal 24, as shown in FIG. 2. These pieces of equipment are housed in a substrate case 25 made of a resin.

Figure 4:
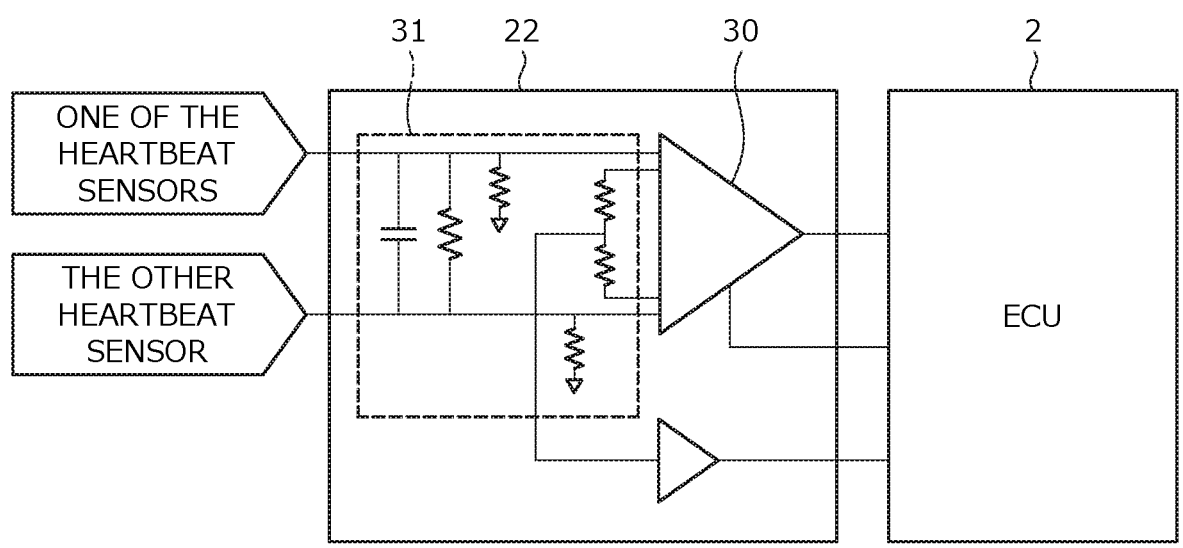
FIG. 4 is a view showing a structure of a circuit substrate.

The circuit substrate 22 is a portion forming a main body of the buffer circuit unit 21. An output signal (an electric signal) from each of the heartbeat sensors 11 is subjected to an amplification processing by this circuit substrate 22. More specifically, the circuit substrate 22 has a differential amplifier 30 as an amplification unit, as shown in FIG. 4. An output signal from each of the heartbeat sensors 11, which has been input to the input terminal 23, is amplified by a function of the differential amplifier 30. In this connection, FIG. 4 is a schematic circuit diagram showing a structure of the circuit substrate 22.

The circuit substrate 22 is provided with an impedance adjustment unit 31 in a preceding stage of the differential amplifier 30, as shown in FIG. 4. This impedance adjustment unit 31 is a circuit for matching an impedance value at a time when one of the right and left pair of heartbeat sensors 11 outputs an electric signal with an impedance value at a time when the other outputs an electric signal.

Incidentally, as shown in FIG. 2, the circuit substrate 22 is in a state sandwiched between the pair of the right and left heartbeat sensors 11 in the seat width direction, and disposed in a gap formed between the heartbeat sensors 11. In this manner, by disposing the circuit substrate 22 utilizing the gap between the heartbeat sensors 11, the present embodiment controls upsizing of the vehicle seat S due to attachment of the circuit substrate 22.

The input terminal 23 is a terminal to which an output signal from each of the heartbeat sensors 11 is input, which is formed of a metal piece. The input terminal 23 is built to both ends of the circuit substrate 22 in the seat width direction. Each input terminal 23 is disposed in a portion adjacent to a base unit 13 of a corresponding heartbeat sensor 11 (strictly, a portion stretched inward in the seat width direction), as shown in FIG. 2. Then, the terminal portion 12a of the leading wire 12 enclosed in the portion adjacent to the input terminal 23 (in other words, the circuit substrate 22) of the base unit 13, is directly connected to the nearest input terminal 23.

That is, in the present embodiment, the terminal portion 12a of the leading wire 12 is connected to an input terminal 23, in a state abutting the input terminal 23. This shortens a transmission path for an output signal from a heartbeat sensor 11, as compared to a case where another leading wire is interposed between the terminal portion 12a of the leading wire 12 and the input terminal 23. As the transmission path is shortened, it becomes hard for a noise to be superposed on an output signal from a heartbeat sensor 11, which improves an accuracy in measuring a heartbeat of a seated person on the basis of the output signal.

In this connection, a method of joining the terminal portion 12a of the leading wire 12 to the input terminal 23 is not particularly limited, but the terminal portion 12a may be joined by using a caulker, or may be joined by using a connector which is not illustrated.

The output terminal 24 is a terminal, from which an electric signal amplified by the differential amplifier 30 is output, which is formed of a metal piece. To this output terminal 24, an end portion of a cable C (strictly, a core material of a cable C) is connected. Accordingly, an electric signal output from the output terminal 24 is transmitted toward the ECU2 through the cable C.

(Guard Ring 15)

The guard ring 15 is a patterned conductor provided in a manner surrounding a heartbeat sensor 11, which controls a leakage current from the heartbeat sensor 11. This guard ring 15 is formed along edge portions of the base film 14 (the inner edge portion and the outer edge portion), over the entire edge portion, as shown in FIG. 2. In the base film 14, in portions corresponding to the linking units 14a and 14b, the guard ring 15 is formed over the entire surface (the front face) of the portions.

Incidentally, in the present embodiment, each of the heartbeat sensors 11, the guard ring 15, and the circuit substrate 22 are disposed in a state horizontally arranged along the seat width direction, as shown in FIG. 2. This makes a space for installing each piece of equipment compact, as compared with a structure in which these pieces of equipment are disposed in a state shifted from each other (strictly, a state shifted in the height direction).

A sensor unit 10A configured as above appropriately detects a body potential of a seated person, when the back of the seated person leans against the seatback S1. Particularly, the sensor unit 10A is disposed in a position where a seated person hardly feels a foreign touch in the seatback S1. More specifically, the buffer circuit unit 21 including the circuit substrate 22 is attached to the front face of the seatback S1 so as to be positioned in the center of the seatback S1 in the seat width direction (illustrated by a broken line in FIG. 2). Since the buffer circuit unit 21 is positioned in the width direction center of the seatback S1 in this manner, it is hard for the buffer circuit unit 21 to touch the back of a seated person, even when the back of the seated person leans against the seatback S1.

Figure 5:
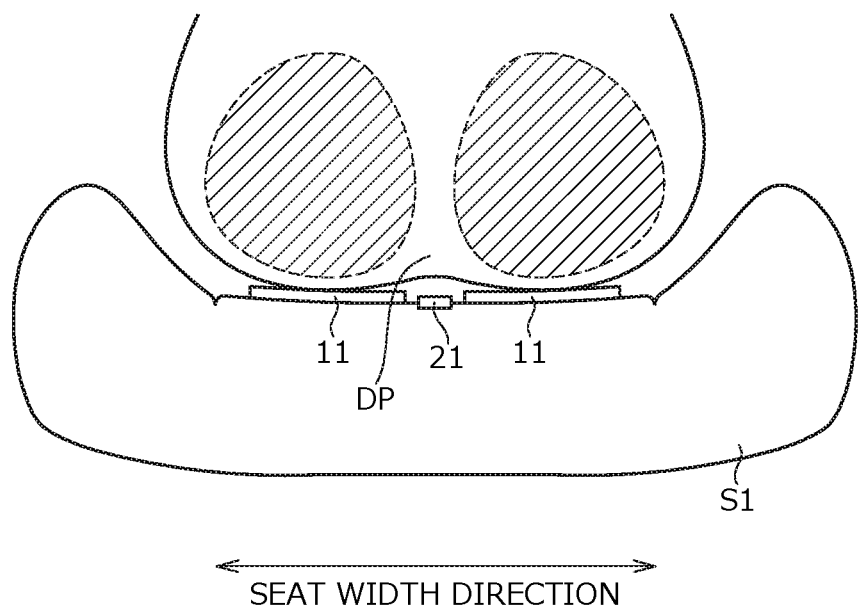
FIG. 5 is a view showing a positional relationship of the back of a seated person, a sensor, and a circuit substrate.

More particularly, when the back of a seated person leans against the seatback S1, the width direction center of the seatback S1 faces a site positioned between a right and left pair of erector spinae (specifically, a portion slightly concaved to the ventral side, which is denoted by sign DP in FIG. 5) of the back of the seated person. FIG. 5 is a schematic view showing a positional relationship of the back of a seated person, the heartbeat sensors 11, and the buffer circuit unit 21, when the back of the seated person leans on the seatback S1. Incidentally, in the figure, the hatched regions correspond to sites corresponding to the erector spinae.

Since the buffer circuit unit 21 is disposed in the width direction center of the seatback S1 as above, it becomes hard for the buffer circuit unit 21 to touch the back (strictly, sites corresponding to the erector spinae) of a seated person, when the back of the seated person leans against the seatback S1.

Incidentally, in the present embodiment, in order to more effectively control the touch of the buffer circuit unit 21 to the back of a seated person, the buffer circuit unit 21 is attached to the front face of the seatback S1 so as to be positioned at a predetermined height in the height direction.

Figure 6:
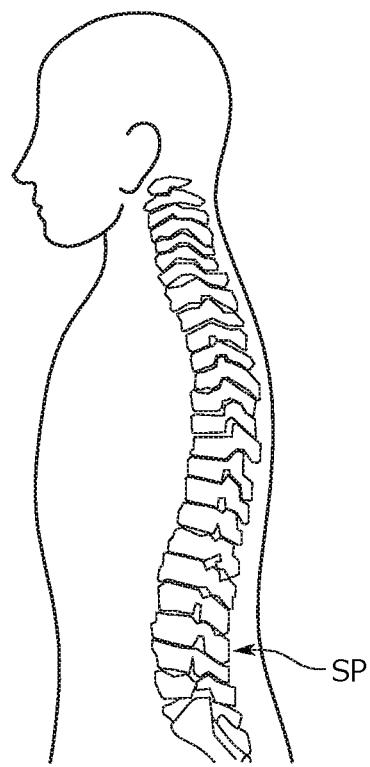
FIG. 6 is a view showing a position of a spinous process in the spine of a seated person.

Specifically, the buffer circuit unit 21 is attached so as to be positioned to a height substantially the same as a height of a site where a spinous process is positioned of the back of a seated person, when the back of the seated person (strictly, a general adult male) leans against the seatback S1. Here, the spinous process refers to a portion curved into a crescent-shape towards the ventral side (the portion denoted by sign SP in FIG. 6), in a spine of a human body. In other words, when the back of a seated person leans against the seatback S1, the site corresponding to the spinous process of the back of the seated person is separated from the seatback S1. FIG. 6 is a view showing a position of a spinous process in the spine of a seated person.

As above, in the present embodiment, the buffer circuit unit 21 is positioned in the center of the seatback S1 in the seat width direction, and disposed in substantially a same position as the spinous process of a seated person in the height direction. In this manner, it becomes hard for the buffer circuit unit 21 to touch the back pf a seated person, when the back of the seated person leans against the seat back S1. As a result, it becomes possible to effectively control the situation that the buffer circuit unit 21 touches the back of a seated person to make the seated person feel a strange touch.

Figure 7:
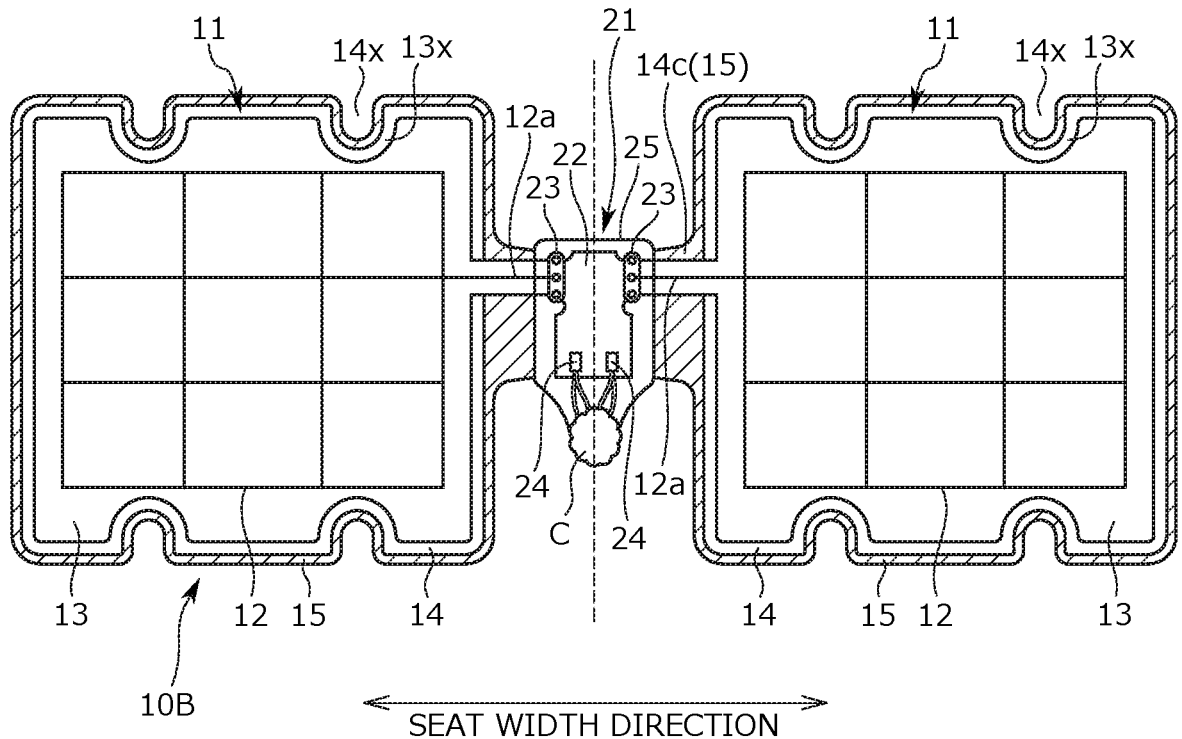
FIG. 7 is a plan view of a sensor and a circuit substrate attached to a seat cushion.

Next, the sensor unit 10B attached to the seat cushion S2 is described with referring to FIG. 7. FIG. 7 is a view of a sensor unit 10B attached to a seat cushion S2, as viewed from above.

The sensor unit 10B has substantially the same structure as that of the sensor unit 10A attached to the seatback S1, except for the point that it is attached to a seat cushion S2. That is, the sensor unit 10B has a right and left pair of heartbeat sensors 11, a buffer circuit unit 21, and a base film 14 on which the heartbeat sensors 11 and the buffer circuit unit 21 are placed, as shown in FIG. 7. In addition, a guard ring 15 is formed on the outer edge portion of the base film 14.

The right and left pair of heart beat sensors 11 is disposed along the upper face (the contact face with a seated person) of a seat cushion S2 via the base film 14. The right and left pair of heartbeat sensors 11 is disposed symmetrically with having the center position of the seat cushion S2 in the seat width direction as a boundary. In addition, the right and left pair of heartbeat sensors 11 is attached to the seat cushion S2 in a state arranged across a predetermined gap in the seat width direction.

Incidentally, a structure of the heartbeat sensor 11 attached to the seat cushion S2 is the same as the aforementioned structure (the structure of the heartbeat sensor 11 attached to the seatback S1), except for the point that the external configuration of the base unit 13 is slightly different as shown in FIG. 7. The following is directed to a structure of a heartbeat sensor 11 attached to a seat cushion S2, in which contents other than the above described contents are omitted.

The base film 14 is used to attach the right and left pair of heartbeat sensors 11 to the upper face (the contact face) of the seat cushion S2. The base film 14 has a long shape which is long in the seat width direction, and on the both ends in the longitudinal direction thereof, the heartbeat sensors 11 are placed, as shown in FIG. 7. Incidentally, the central portion in the longitudinal direction of the base film 14 is narrowed in the front to back direction, so as to have a slightly narrower width than the both end portions in the longitudinal direction. The central portion in the longitudinal direction of the base film 14 functions as a linking unit 14c which links between the heartbeat sensors 11. However, this is not a limitation, and it is also possible that the linking unit 14c is not formed, and the right and left pair of heartbeat sensors 11 is separately attached to the seat cushion S2.

The buffer circuit unit 21 has a circuit substrate 22, an input terminal 23, an output terminal 24, and a substrate case 25 for housing them. As for circuit structure of the circuit substrate 22, explanation will be omitted, because it is the same as that of the circuit substrate 22 of the buffer circuit unit 21 attached to the seatback S1.

As shown in FIG. 7, the circuit substrate 22 is in a state sandwiched between the pair of the right and left heartbeat sensors 11 in the seat width direction, and disposed in a gap formed between the heartbeat sensors 11. Each of the input terminals 23 built on the both ends in the seat width direction of the circuit substrate 22 is disposed in a position adjacent to a base unit 13 of a corresponding heartbeat sensor 11 (strictly, a portion stretched inward in the seat width direction), as shown in FIG. 7.

In a base unit 13, a terminal portion 12a of a leading wire 12 enclosed in the portion adjacent to an input terminal 23 (namely, the circuit substrate 22) is directly connected to the nearest input terminal 23. This makes a transmission path for an output signal from a heartbeat sensor 11 as short as possible also in the sensor unit 10B attached to the seat cushion S2, and accordingly, it becomes hard for a noise to be superposed on an output signal from a heartbeat sensor 11. This improves, as a result, an accuracy in measuring heartbeat of a seated person on the basis of an output signal from a heartbeat sensor 11 attached to a seat cushion S2.

The guard ring 15 is formed along the outer edge portion of the base film 14, over the entire periphery of the outer edge portion. On the linking unit 14c provided to the central portion in the seat width direction of the base film 14, the guard ring 15 is formed over the entire surface (the upper face) of the portion.

Incidentally, as shown in FIG. 7, each of the heartbeat sensors 11, the guard ring 15, and the circuit substrate 22 are disposed in a horizontal arrangement along the seat width direction, also in the sensor unit 10B attached to the seat cushion S2, similarly as in the sensor unit 10A attached to the seatback S1. This makes a space for installing each piece of the equipment compact.

A sensor unit 10B configured as above appropriately detects a body potential of a seated person, when the buttocks of the seated person are put on the seat cushion S2. Particularly, the sensor unit 10B is disposed in a position where a seated person hardly feels a strange touch in the seat cushion S2. More specifically, the buffer circuit unit 21 including the circuit substrate 22 is attached to the upper face of the seat cushion S2 so as to be positioned in the center of the seat cushion S2 in the seat width direction (illustrated by a broken line in FIG. 7).

The buffer circuit unit 21 is attached on the upper face of the seat cushion S2 so as to be within a predetermined range in the front to back direction. Specifically, the buffer circuit unit 21 is attached so as to be within a range where the gluteal cleft portion (intergluteal cleft) of a seated person is positioned, in the front to back direction, when the buttocks of a seated person (strictly, a general adult male) are put on the seat cushion S2. Here, the gluteal cleft portion refers to a portion concaved toward the ventral side, in the buttocks of a human body. In other words, when the buttocks of a seated person are put on the seat cushion S2, a site corresponding to the gluteal cleft portion is separated from the seat cushion S2.

As above, in the present embodiment, the buffer circuit unit 21 is positioned in the center of a seat cushion S2, in the seat width direction, and disposed within the range where the gluteal cleft portion of a seated person is positioned, in the front to back direction. This makes it hard for the buffer circuit unit 21 to touch the buttocks of a seated person when the buttocks of the seated person are put on the seat cushion S2, to allow effectively controlling a situation that a seated person feels a strange touch due to a touch of the buffer circuit unit 21 to the buttocks of the seated person.

Figure 8:
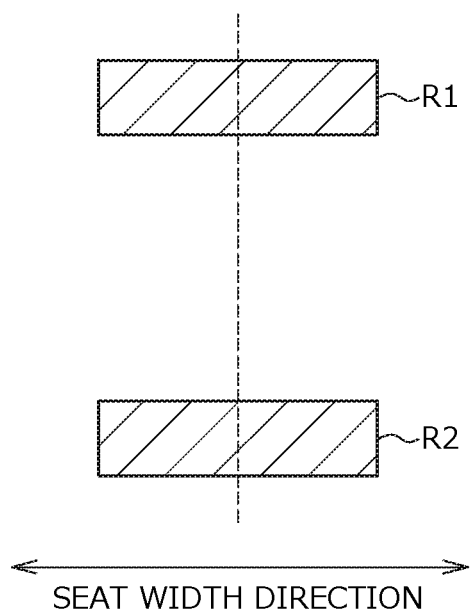
FIG. 8 is a view showing a location range of a circuit substrate in each of a seatback and a seat cushion.

In addition, in the present embodiment, a range in which the circuit substrate 22 attached to the seatback S1 is present in the seat width direction (represented by R1 in the figure), and a range in which the circuit substrate 22 attached to the seat cushion S2 is present in the width direction (represented by R2 in the figure) are overlapped with each other, as shown in FIG. 8. FIG. 8 is a schematic view showing the ranges for the circuit substrate 22 to be present in each of the seatback S1 and the seat cushion S2.

In the present embodiment, it becomes possible to properly fit the circuit substrate 22 to each of the seat cushion and the seatback, for the above positional relationship. As a result, when each circuit substrate 22 is attached, the attachment work thereof become performed comparatively easily. Incidentally, in the structure illustrated in FIG. 8, the range R1 in which a circuit substrate 22 attached to the seatback S1 is present, and the range R2 in which a circuit substrate 22 attached to the seat cushion S2 is present completely coincide with each other in the seat width direction, however, this is not a limitation, and the ranges only need to overlap with each other at least a partially.

Modification Example of Sensor Unit

In the above described embodiment, an example of sensor unit was referred to for the explanation. However, the structure of the sensor unit described above is merely an example, and other examples are also conceivable. Below described is a sensor units 100A and 100B according to a second embodiment (hereinbelow, a modification example) of the present invention. The modification example differs from the embodiment described above in terms of structure of the sensor units 100A and 100B, but the modification example and the previous embodiment have the other points in common. That is, a bioinformation measurement device according to the modification example has the same function as the bioinformation measurement device according to the previous embodiment has, and achieves the same effect as brought about by the function.

Figure 9:
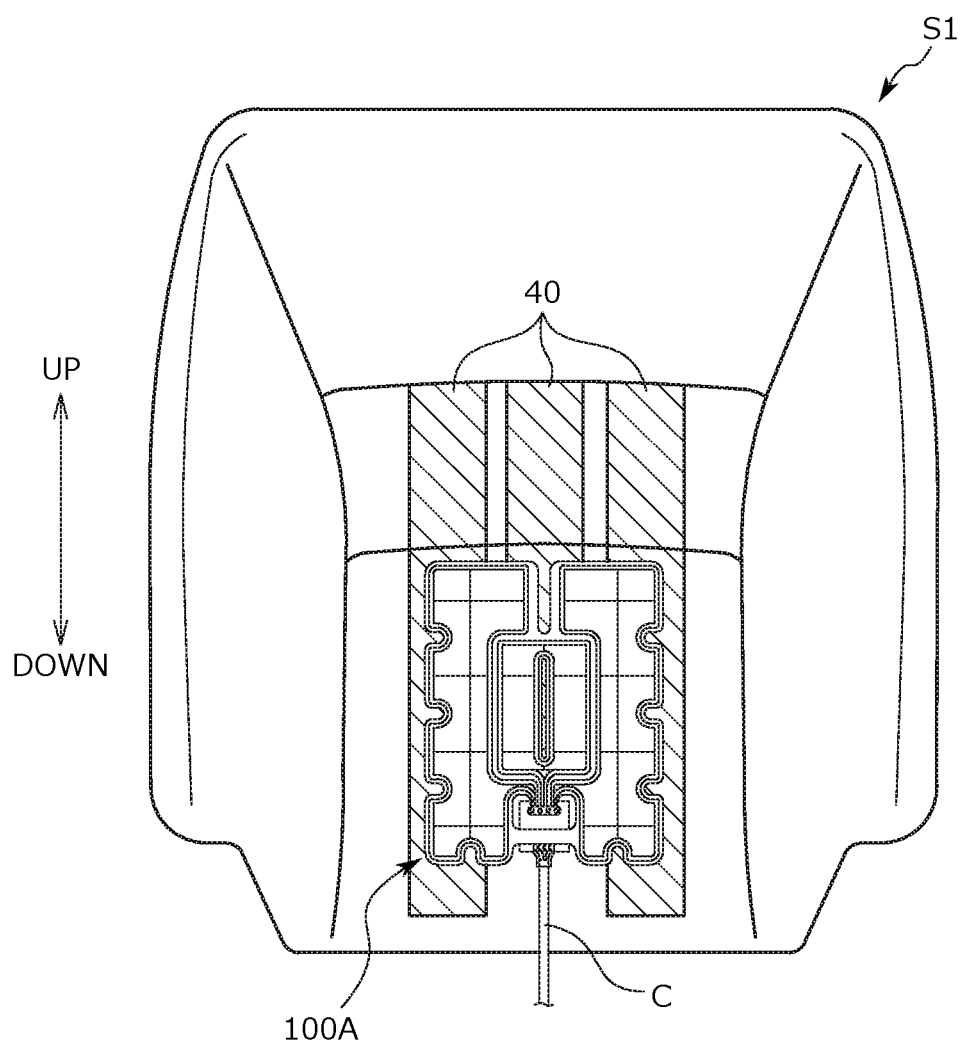
FIG. 9 is a view showing a seatback of a vehicle seat according to a second embodiment of the present invention.
Figure 10:
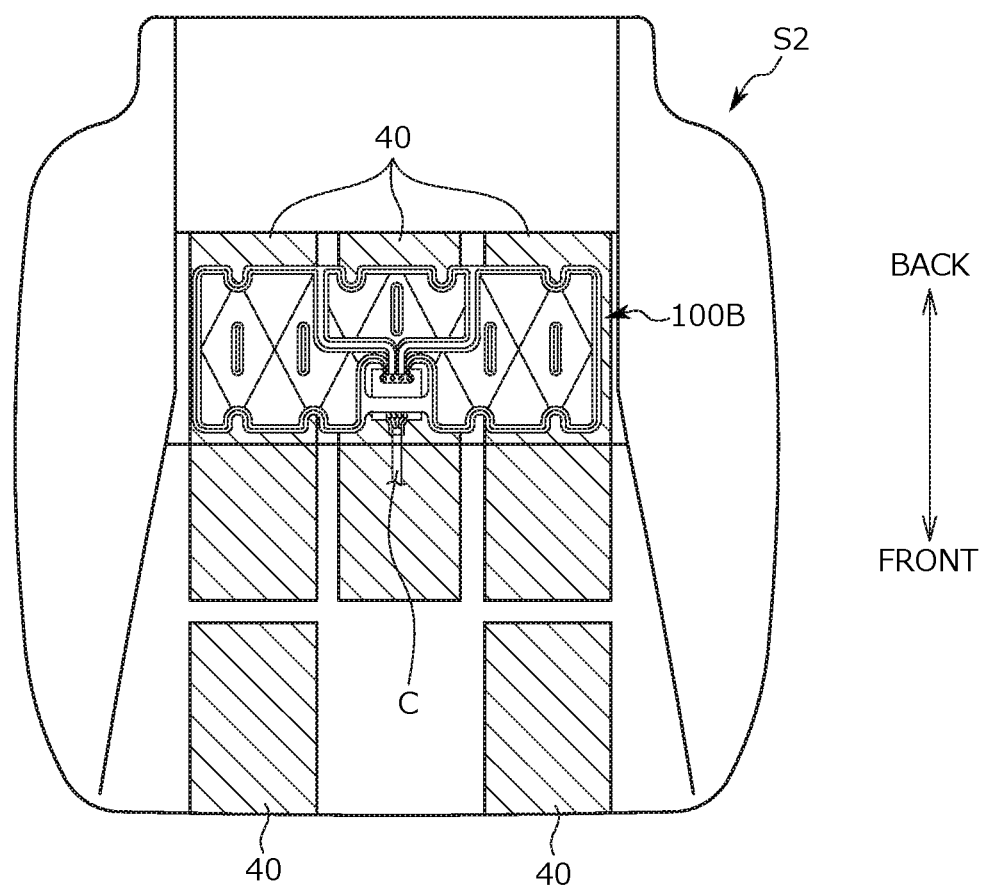
FIG. 10 is a view showing a seat cushion of a vehicle seat according to a second embodiment of the present invention.

In the modification example, a sensor unit 100A is disposed in the seatback S1, as shown in FIG. 9. In addition, a sensor unit 100B is disposed in the seat cushion S2, as shown in FIG. 10. FIG. 9 and FIG. 10 are explanatory views of the sensor units 100A and 100B according to the modification example, and FIG. 9 is a view of the seat back S1 as viewed from the front (ahead), and FIG. 10 is a view of the seat cushion S2 as viewed from above.

Positions to dispose each of the sensor units 100A and 100B are substantially the same positions as the positions to dispose the sensor units 10A and 10B in the previous embodiment (the embodiment illustrated in FIG. 2). In the modification example, a conductive cloth 40 having a shape of rectangular belt is disposed on the backside of each sensor unit 100A and 100B. The conductive cloth 40 is made of a material publicly known as a conductive cloth, and sewed together with a skin material constituting the seatback S1 or the seat cushion S2 along the edge of the conductive cloth 40.

A position to dispose the conductive cloth 40 is particularly described. Three conductive cloths 40 are disposed in the central portion in the seat width direction of the backrest face (the front face) of the seatback S1, as shown in FIG. 9. These three conductive cloths 40 are disposed symmetrically with respect to the center in the seat width direction of the seatback S1. The sensor unit 100A in the side of the seatback S1 is disposed in such a position that the sensor unit 100A is put across all the three conductive cloths 40 in the seat width direction. In other words, the sensor unit 100A in the side of the seatback S1 is disposed so as to span all the three conductive cloths 40.

In addition, each of the three conductive cloths 40 is formed so as to have a uniform length in the seat width direction (width). On the other hand, the center conductive cloth 40 of the three conductive cloths 40 is made shorter than the other two conductive cloths 40. More particularly, each of the three conductive cloths 40 is disposed such that the individual upper ends are lined up in the height direction. The individual upper ends of the three conductive cloths 40 are positioned somewhat upper than the upper end of the sensor unit 100A, as shown in FIG. 9. On the other hand, the lower end of the center conductive cloth 40 of the three conductive cloths 40 is positioned somewhat upper than the lower ends of the other two conductive cloths 40.

Position to dispose the conductive cloth 40 in the seat cushion S2 is described. On the seating face (the upper face) of the seat cushion S2, five conductive cloths 40 are disposed in the central portion in the seat width direction of the seat cushion S2, as shown in FIG. 10. More particularly, the five conductive cloths 40 are disposed symmetrically with respect to the center in the seat width direction of the seat cushion S2. Two of the five conductive cloths 40 (hereinbelow, conductive cloths 40 in the front row) are disposed in the front end portion of the seat cushion S2, and the other three (hereinbelow, conductive cloths 40 in the back row) are disposed in positions slightly rearward of the conductive cloths 40 in the front row. The sensor unit 100B in the side of the seat cushion S2 is disposed in such a position that the sensor unit 100B is put across all of the conductive cloths 40 in the back row in the seat width direction. In other words, the sensor unit 100B in the side of the seat cushion S2 is disposed so as to span all the conductive cloths 40 in the back row.

Each of the five conductive cloths 40 is formed so as to have a uniform length in the seat width direction (width). Further, each of the conductive cloths 40 in the back row is disposed such that the individual front ends are lined up in the front to back direction. Incidentally, the front end of each of the conductive cloths 40 in the back row is positioned somewhat forward of the front end of the sensor unit 100B, as shown in FIG. 10. On the other hand, the front end portion of each of the conductive cloths 40 in the front row goes around to the front end face of the seat cushion S2.

Figure 11:
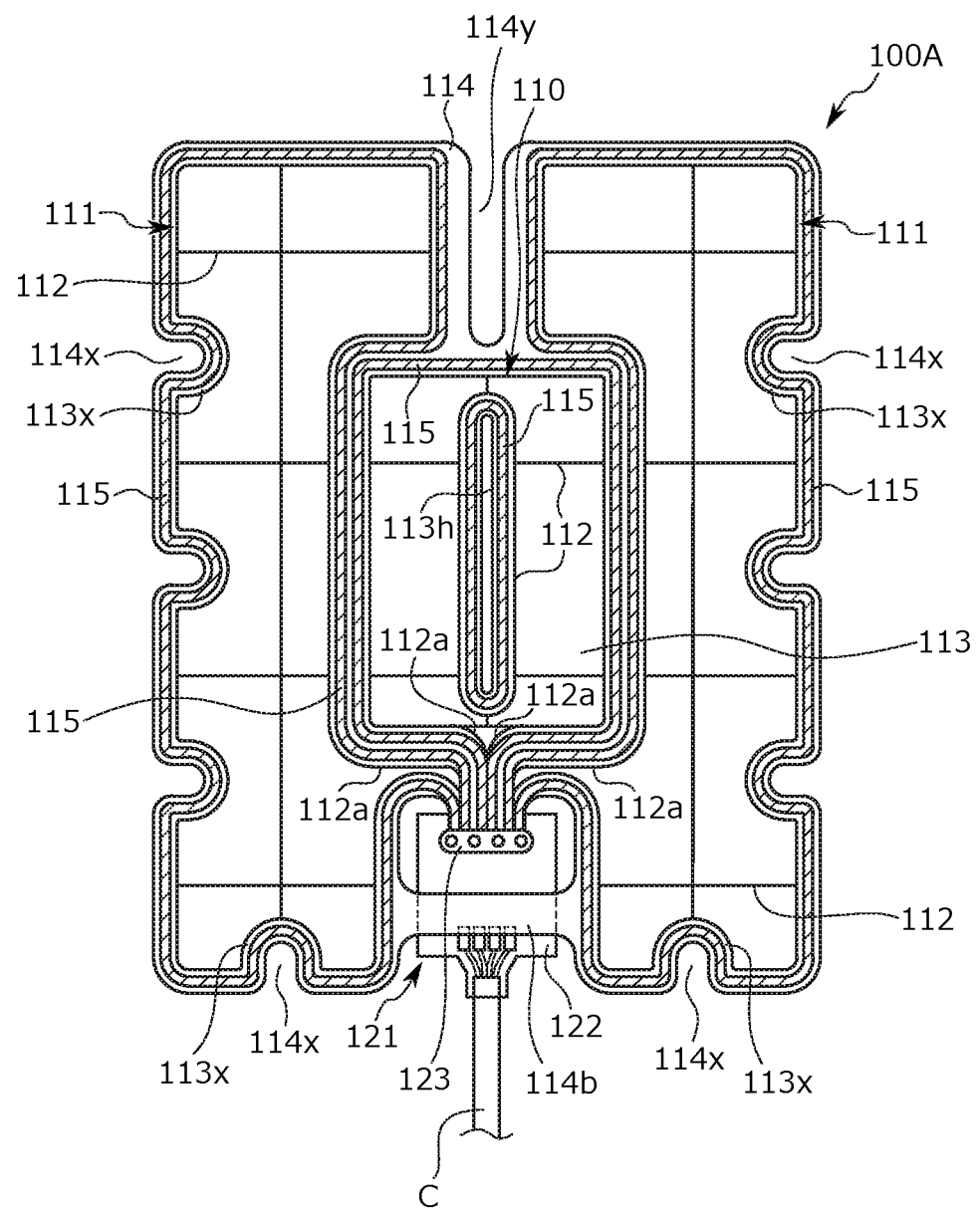
FIG. 11 is a view showing a sensor and a circuit substrate in the side of the seat back, according to a second embodiment of the present invention.

Below described are structures of the sensor units 100A and 100B according to the modification example. First, a structure of the sensor unit 100A in the side of the seatback S1 is described with referring to FIG. 11. FIG. 11 is a view of the sensor unit 100A in the side of the seatback S1, as viewed from the front (ahead).

The sensor unit 100A has a ground electrode unit 110, a right and left pair of heartbeat sensors 111, a buffer circuit unit 121, and a base film 114, as shown in FIG. 11. In addition, a guard ring 115 is formed on the base film 114.

The ground electrode unit 110 regulates a reference potential (namely, 0 V) at the time of detecting a body potential of a seated person by the heartbeat sensor 111, and is disposed in a position sandwiched between the right and left pair of heartbeat sensors 111. This ground electrode unit 110 is used for the purpose of confirming a potential difference with the heartbeat sensor 111, and for the purpose of controlling occurrence of noise caused by static electricity or the like. Structure of the ground electrode unit 110 is the same as that of the heartbeat sensor 111. Particularly, the ground electrode unit 110 is formed of an electrode in a shape of a sheet, and has a substantially rectangular external configuration, as shown in FIG. 11. Incidentally, as illustrated in FIG. 9, the ground electrode unit 110 is disposed such that the center position in the right to left direction coincides with the center position in the seat width direction of seatback S1.

The ground electrode unit 110 is formed of the leading wire 112 and the base unit 113 which encloses the leading wire 112. The base unit 113 has a laminated structure similar to that of the base unit 13 of the heartbeat sensor 11 according to the previous embodiment (the laminated structure as illustrated in FIG. 3). In the central portion of the base unit 113, a long hole 113h elongated in the vertical direction is formed. The leading wire 112 is wired regularly in the base unit 113. Specifically, the leading wire 112 constituting the ground electrode unit 110 has a portion wired along the edge of the ground electrode unit 110 which has a substantially rectangular shape, a portion wired in a manner surrounding the long hole 113h described above, and a portion wired to interlink these portions, along the vertical direction or the seat width direction. In the leading wire 112, a terminal portion 112a which is the most downwardly positioned extends downward toward the buffer circuit unit 121, as shown in FIG. 11. Then, the terminal portion 112a of the leading wire 112 is joined to an input terminal 123 of a circuit substrate 122 provided to the buffer circuit unit 121.

The right and left pair of heartbeat sensors 111 is disposed symmetrically with having the center position in the seat width direction of the seatback S1 as a boundary, and sandwiches the ground electrode unit 110 therebetween. More particularly, the right and left pair of heartbeat sensors 111 forms an external configuration of approximate C-letter shapes facing each other. The ground electrode unit 110 is disposed between the right and left pair of heartbeat sensors 111 which is accordingly disposed in a manner surrounding the four sides of the ground electrode unit 110.

A structure of the heartbeat sensor 111 according to the modification example is described. Each of the heartbeat sensors 111 is formed of a leading wire 112 and a base unit 113 that encloses the leading wire 112, similarly as the heartbeat sensor 11 according to the previous embodiment. The base unit 113 is a sheet-shaped member which defines an outer shape of the heartbeat sensor 111, and has the same laminated structure as that of the base unit 13 of the heartbeat sensor 11 according to the previous embodiment (the laminated structure illustrated in FIG. 3). Arcuate notches 113x are formed in predetermined portions in the outer edge portion of the base unit 113 (specifically, the end portion in the outer side in the seat width direction, and the lower end portion). In this manner, the base unit 113 bends without accompanied by a wrinkle, when the back of a seated person leans against the seatback S1. This suppresses, as a result, an influence to the heartbeat sensor 111 given when the back of a seated person leans against the seatback S1 (specifically, a bend of the leading wire 112, and a disconnection caused thereby).

A leading wire 112 constituting a heartbeat sensor 111 has a portion wired along the edge of the heartbeat sensor 111 in the base unit 113, and a portion wired in a lattice shape inside the portion. In the leading wire 112 wired along the edge of heartbeat sensor 111, a portion positioned in the inner end portion in the seat width direction of the heartbeat sensor 111 is bent along the periphery of the ground electrode unit 110, in a manner deflecting from the ground electrode unit 110, as shown in FIG. 11. A portion of the leading wire 112 wired along the edge of the heartbeat sensor 111 (more strictly, the leading wire 112 positioned in the inner end portion in the seat width direction of the heartbeat sensor 111) constitutes a terminal portion 112a. As shown in FIG. 11, the terminal portion 112a goes around to the lower position of the ground electrode unit 110, and extends curvedly downward toward the buffer circuit unit 121, to finally join to the input terminal 123 of the circuit substrate 122 which is provided to the buffer circuit unit 121.

The base film 114 is a substrate in a shaped of a sheet for attaching the ground electrode unit 110 and each of the right and left pair of heartbeat sensors 111 to the front face (the backrest face) of the seatback S1. In the modification example, the base film 114 for attaching the ground electrode unit 110, and the base film 114 for attaching each of the heartbeat sensors 111 are continuous and integrated into a sheet as a whole.

The base film 114 according to the modification example is molded into an approximate H-letter shape. The heartbeat sensors 111 are adhered to the front face of the side portions (the vertically long portions) of the H-letter shaped base film 114, and the ground electrode unit 110 is adhered to the front face of the central portion. As above, in the modification example, the ground electrode unit 110 and the right and left pair of heartbeat sensors 111 form a unit by being adhered to the single sheet of base film 114.

Incidentally, in the base film 114, a notch with a vertically long slit-shape (hereinbelow, vertical notch 114y) is formed between the upper end portion of the portion to which the left heartbeat sensor 111 is adhered and the upper end portion of the portion to which the right heartbeat sensor 111 is adhered. In addition, in the edge portion of the base film 114, in portions adjacent to the notches 113x formed on the base unit 113 of the heartbeat sensor 111, similarly arcuate notches 114x are formed. Specifically, as shown in FIG. 11, a notch 114x is formed in the lower end portion of a portion to which a heartbeat sensor 111 is adhered, of the base film 114. In addition, three notches 114x arranged in the vertical direction are formed in a side end portion (strictly, an outer end portion in the seat width direction) of a portion to which a heartbeat sensor 111 is adhered. Incidentally, among the three notches 114x arranged in the vertical direction, the notch 114x in the uppermost position is formed in the same position as that of the lower end portion of the aforementioned vertical notch 114y, in the height direction. That is to say, the vertical notch 114y is formed so as to reach the position in which the uppermost position notch 114x is formed, in the height direction.

In the base film 114, the lower end portion of the portion to which the left side heartbeat sensor 111 is adhered, and the lower end portion of the portion to which the right side heartbeat sensor 111 is adhered are separated from each other in the seat width direction. In the modification example, the buffer circuit unit 121 is disposed, utilizing a space between the separated lower end portions, as shown in FIG. 11. Incidentally, the buffer circuit unit 121 disposed in the space is positioned inner than the outermost portion of the outer edge of the base film 114, as shown in FIG. 11. As also shown in the same figure, the base film 114 is provided with a linking unit 114*b* that interlinks between the separated lower end portions.

The guard ring 115 is formed on the base film 114, in a manner surrounding the ground electrode unit 110 and each of the right and left pair of heartbeat sensors 111. More specifically, the guard ring 115 disposed around the heartbeat sensor 111 is formed over the entire periphery of the edge of the base unit 113 of the heartbeat sensor 111. The guard ring 115 disposed around the ground electrode unit 110 is formed over the entire periphery of the edge of the base unit 113 of the ground electrode unit 110. In the ground electrode unit 110, the guard ring 115 is also formed around the long hole 113*h*, as shown in FIG. 11.

The buffer circuit unit 121 is positioned between the right and left pair of heartbeat sensors 111, and at the same time, disposed in a lower position from the ground electrode unit 110. More specifically, the buffer circuit unit 121 is disposed between the lower end portion of the portion to which the left side heartbeat sensor 111 is adhered and the lower end portion of the portion to which the right side heartbeat sensor 111 is adhered, in the base film 114. Incidentally, in the position in which the buffer circuit unit 121 is disposed, the linking unit 114*b* of the base film 114 is provided. Strictly, in the modification example, the buffer circuit unit 121 is disposed in the rear side (the backside) of the linking unit 114*b*, as shown in FIG. 11. This allows the linking unit 114*b* to function as a controlling unit that controls a forward movement of the buffer circuit unit 121.

Figure 12:
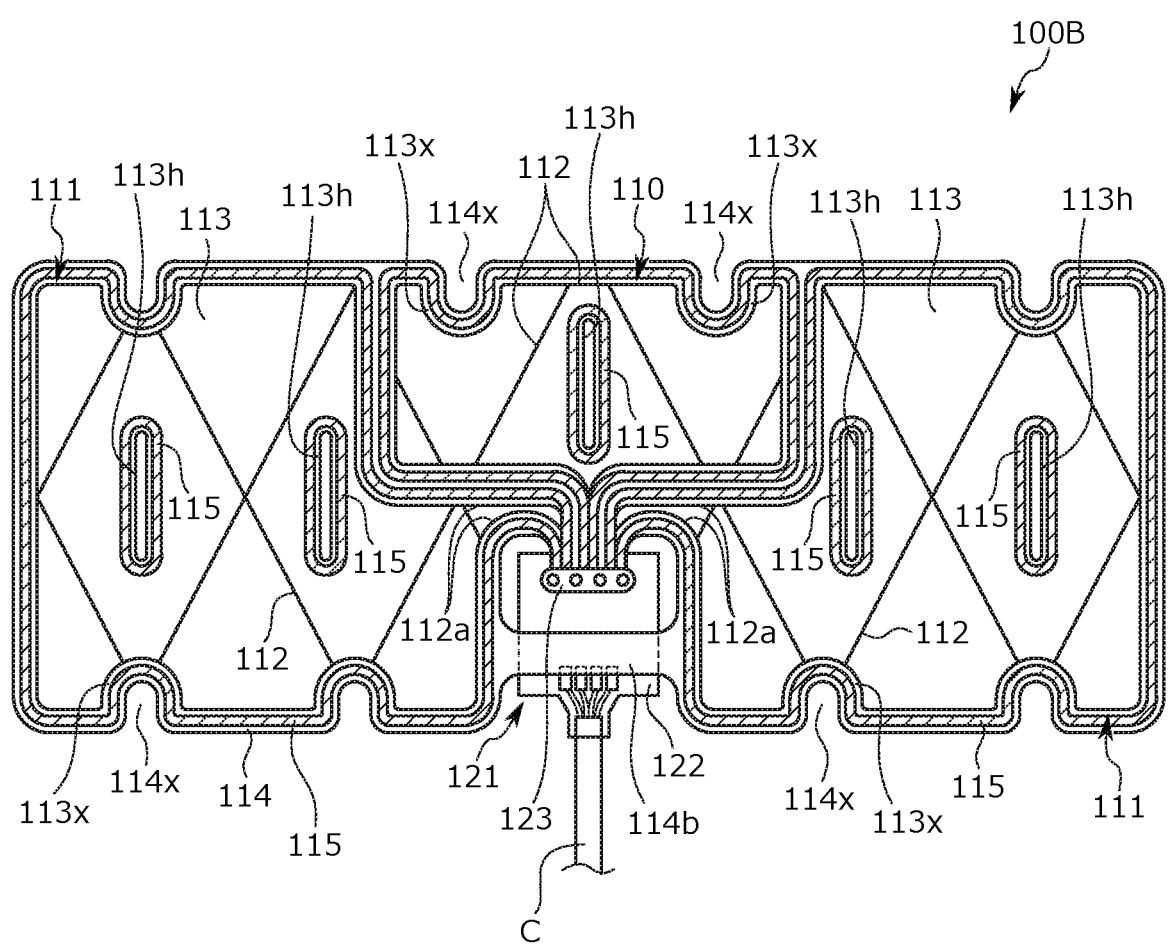
FIG. 12 is a view showing a sensor and a circuit substrate in the side of the seat cushion according to a second embodiment of the present invention.

Next, a structure of the sensor unit 100B in the side of the seat cushion S2 is described with referring to FIG. 12. FIG. 12 is a view of a sensor unit 100B in the side of the seat cushion S2, as viewed from above.

The sensor unit 100B basically has the same structure as that of the sensor unit 100A attached to the seatback S1, except for the point that it is attached to a seat cushion S2. That is, the sensor unit 100B has a ground electrode unit 110, a right and left pair of heartbeat sensors 111, a buffer circuit unit 121, and a base film 114, as shown in FIG. 12. In addition, a guard ring 115 is formed on the base film 114. These unit components have the same structures as those of the parts constituting the sensor unit 100A in the side of the seatback S1, except for shapes or disposed positions.

The ground electrode unit 110 has a horizontally long rectangular shape as illustrated in FIG. 12. As illustrated in FIG. 10, the ground electrode unit 110 is disposed such that the center position in the right to left direction thereof coincides with a center position in the seat width direction of seat cushion S2. In the central portion of a base unit 113 constituting the ground electrode unit 110, a long hole 113*h* elongated in the front to back direction is formed. A leading wire 112 enclosed in the base unit 113 is wired in a zigzag manner. Incidentally, in the leading wire 112, the terminal portion 112*a* positioned immediately before the long hole 113*h* extends forward toward the buffer circuit unit 121, and joins to the input terminal 123 of the circuit substrate 122 in the buffer circuit unit 121.

Furthermore, arcuate notches 113*x* are formed in a rear end portion of the base unit 113. This allows the base unit 113 to bend without being accompanied by a wrinkle, when the buttocks of a seated person are put on the seat cushion S2. As a result, an influence to the ground electrode unit 110 given when a seated person is seated on the seat cushion S2 (specifically, a bend of the leading wire 112, and a disconnection caused thereby) is suppressed.

The right and left pair of heartbeat sensors 111 is disposed symmetrically with having the center position in the seat width direction of the seat cushion S2 as a boundary, and sandwiches the ground electrode unit 110 therebetween. More particularly, the right and left pair of heartbeat sensors 111 forms an external configuration of approximate L-letter shapes facing each other. Then, between the rear end portions of the heartbeat sensors 111, the ground electrode unit 110 is disposed, as shown in FIG. 12.

In addition, arcuate notches 113*x* are formed on predetermined portions in edge portions, specifically, in the fore end portion and the rear end portion, of the base unit 113 which constitutes each of the heartbeat sensors 111. Such notches 113*x* achieve the same effect as that achieved by the notch 113*x* provided to the base unit 113 of the ground electrode unit 110 described above. Inner side portion of the base unit 113 of each of the heartbeat sensors 111, a long hole 113*h* elongated in the front to back direction is formed. This long hole 113*h* is formed in substantially the same position as the position in which the notch 113*x* is formed, in the seat width direction, as shown in FIG. 12.

The leading wire 112 constituting the heartbeat sensor 111 has a portion wired along the edge of a heartbeat sensor 111 in the base unit 113, and inside the portion, a portion wired in an X-letter shape. Incidentally, in the leading wire 112 wired along the edge of a heartbeat sensor 111, the portions positioned in the inside end portion in the seat width direction of the heartbeat sensor 111 are bent along the periphery of the ground electrode unit 110, in a manner deflecting from the ground electrode unit 110, as shown in FIG. 12. A portion of the leading wire 112 wired along the edge of a heartbeat sensor 111 (more strictly, the leading wire 112 positioned at the inside end portion in the seat width direction of the heartbeat sensor 111) constitutes a terminal portion 112*a*. Then, as shown in FIG. 12, the terminal portion 112*a* goes around to the fore position of the ground electrode unit 110, extends curvedly forward toward the buffer circuit unit 121, and finally joins to an input terminal 123 of the circuit substrate 122 in the buffer circuit unit 121.

The base film 114 is formed of a sheet, in which a portion to which the ground electrode unit 110 is adhered, and portions to which the heartbeat sensors 111 are adhered are continuous and integrated. The base film 114 is shaped into an approximate downward U-letter shape. The heartbeat sensors 111 are adhered to the upper face of the side portions of the downward U-letter shaped base film 114, and the ground electrode unit 110 is adhered to the upper face of the central portion. In addition, in the edge portion of the base film 114, in portions adjacent to the notches 113*x* formed on the base unit 113 of the ground electrode unit 110 and the heartbeat sensor 111, similarly arcuate notches 114*x* are formed.

In the base film 114, the fore end portion of the portion to which the left side heartbeat sensor 111 is adhered, and the fore end portion of the portion to which the right side heartbeat sensor 111 is adhered are separated from each other in the seat width direction. Then, as shown in FIG. 12, the buffer circuit unit 121 is disposed, utilizing a space between the separated fore end portions. Incidentally, the buffer circuit unit 121 disposed in the above described space is positioned inward to the outermost portion of the outer edge of the base film 114, as shown in FIG. 12. As also shown in the same figure, the base film 114 is provided with a linking unit 114*b* that interlinks between the separated fore end portions. By disposing the buffer circuit unit 121 in the lower side (the backside) of this linking unit 114*b*, an upward movement of the buffer circuit unit 121 is controlled by the linking unit 114*b*.

The guard ring 115 is formed over the entire periphery of the edge of the base unit 113 of each of the ground electrode unit 110 and the heartbeat sensors 111, and at the same time, formed also around the long holes 113h provided to the inner side region of each of the base units 113.

The Other Embodiments

In the embodiment described above, a structure of the bioinformation measurement device of the present invention has been described with referring to an example. However, the embodiment described above does not limit the present invention, but is merely an example for facilitating understanding of the present invention. That is, the present invention may be modified or improved without deviated from the gist thereof, and the present invention naturally involves equivalents thereof.

In the above described embodiment, a heartbeat was measured as a bioinformation of a seated person. However, this is not a limitation, and the present invention may also be applied to a case where a bioinformation other than a heartbeat, such as a body temperature, a brain wave, a respiration waveform or the like is measured.

In the above described embodiment, the circuit substrate 22 was provided therein with the differential amplifier 30 that amplified an output signal (an electric signal) from a heartbeat sensor 11, and at the same time, provided with the impedance adjustment unit 31 for adjusting impedance values between the heartbeat sensors 11. However, this is not a limitation, and the structure may also be such that only the differential amplifier 30 is provided, and the impedance adjustment unit 31 is not provided in the circuit substrate 22.

In addition, in the above described embodiment, the wiring pattern of the leading wire 12 in a heartbeat sensor 11 was described with referring to an example (specifically, the example illustrated in FIG. 2 or FIG. 7). However, a wiring pattern of the leading wire 12 may arbitrarily be set, as long as it can preferably detect a body potential of a seated person.

In the embodiment described above, a right and left pair of heartbeat sensors 11 was attached individually to the seatback S1 and the seat cushion S2. However, number of the heartbeat sensor 11 is not particularly limited, and the structure may be such that each one heartbeat sensor 11 is attached to the seatback S1 and the seat cushion S2. The structure may also be such that a heartbeat sensor 11 is attached only to the seatback S1.

REFERENCE SIGNS LIST

1: Heartbeat measurement device (Bioinformation measurement device)
10A, 10B, 100A, 100B: Sensor unit
11, 111: Heartbeat sensor (Sensor)
12, 112: Leading wire
12a, 112a: Terminal portion
13, 113: Base unit
13a: Lowermost layer
13b: Intermediate layer
13c: Uppermost layer
13x, 113x: Notch
14, 114: Base film
14a, 14b, 14c, 114b: Linking unit
14x, 114x: Notch
114y: Vertical notch
15, 115: Guard ring
21, 121: Buffer circuit unit
22, 122: Circuit substrate
23, 123: Input terminal
24: Output terminal
25: Substrate case
30: Differential amplifier (Amplification unit)
31: Impedance adjustment unit
40: Conductive cloth
110: Ground electrode unit
113h: Long hole
C: Cable
S: Vehicle seat (Seat)
S1: Seatback
S2: Seat cushion
S3: Headrest

The invention claimed is:

1. A device comprising:
a seat;
a bioinformation measurement device for measuring a bioinformation of a seated person who is seated on the seat, wherein
the bioinformation measurement device comprises:
a sensor which outputs an electric signal according to the bioinformation, and comprises a leading wire including a transmission path for the electric signal, and
a circuit substrate comprising an input terminal connected to the leading wire of the sensor and configured to receive the electric signal from the sensor, and an amplification unit configured to amplify the electric signal input to the input terminal,
the sensor and the circuit substrate are arranged on a contact face of the seat, which comes in contact with the seated person, and disposed in positions adjacent to each other in a width direction of the seat, and
a terminal portion of the leading wire extends from a portion of the sensor adjacent to the circuit substrate and is connected to the input terminal in a state abutting the input terminal.

2. The device according to claim 1, wherein the circuit substrate is attached to the seat to be positioned at a center of the seat in the width direction of the seat.

3. The device according to claim 1, wherein
the bioinformation measurement device further comprises a plural number of the sensor,
the plural number of the sensor are arranged across a gap in the width direction of the seat, and
the circuit substrate is disposed within the gap in a state sandwiched between the sensors.

4. The device according to claim 1, wherein the bioinformation measurement device further comprises a guard ring disposed in a manner surrounding the sensor, and
the sensor, the guard ring, and the circuit substrate are disposed in a state arranged along the width direction of the seat.

5. The device according to claim 1, wherein the seat comprises a seatback, and
the circuit substrate is attached to the seatback to be positioned at a center of the seatback in the width direction of the seat.

6. The device according to claim 1, wherein the seat comprises a seat cushion, and
the circuit substrate is attached to the seat cushion to be positioned at a center of the seat cushion in the width direction of the seat.

7. The device according to claim 1, wherein the seat comprises a seat cushion and a seatback, the sensor and the circuit substrate are attached to each of the seat cushion and the seatback, and a range where the circuit substrate attached to the seat cushion is present in the width direction of the seat, and a range where the circuit substrate attached to the seatback is present in the width direction of the seat, overlap with each other in the width direction of the seat.

8. A device, comprising:

a seat;

a bioinformation measurement device for measuring a bioinformation of a seated person who is seated on the seat, wherein the bioinformation measurement device comprises:

- a sensor which outputs an electric signal according to the bioinformation, and comprises a leading wire including a transmission path for the electric signal;
- a circuit substrate comprising an input terminal connected to the leading wire of the sensor and configured to receive the electric signal from the sensor, and an amplification unit configured to amplify the electric signal input to the input terminal; and
- a guard ring disposed in a manner surrounding the sensor, the sensor and the circuit substrate are disposed in positions adjacent to each other in the seat, a terminal portion of the leading wire extends from a portion of the sensor adjacent to the circuit substrate and is connected to the input terminal in a state abutting the input terminal, and the sensor, the guard ring, and the circuit substrate are disposed in a state arranged along a width direction of the seat.

9. The device according to claim 8, wherein the circuit substrate is attached to the seat to be positioned at a center of the seat in the width direction of the seat.

10. The device according to claim 8, wherein the bioinformation measurement device further comprises a plural number of the sensor, the plural number of the sensor are arranged across a gap in the width direction of the seat, and the circuit substrate is disposed within the gap in a state sandwiched between the sensors.

11. The device according to claim 8, wherein the seat comprises a seatback, and the circuit substrate is attached to the seatback to be positioned at a center of the seatback in the width direction of the seat.

12. The device according to claim 8, wherein the seat comprises a seat cushion, and the circuit substrate is attached to the seat cushion to be positioned at a center of the seat cushion in the width direction of the seat.

13. The device according to claim 8, wherein the seat comprises a seat cushion and a seatback, the sensor and the circuit substrate are attached to each of the seat cushion and the seatback, and a range where the circuit substrate attached to the seat cushion is present in the width direction of the seat, and a range where the circuit substrate attached to the seatback is present in the width direction of the seat, overlap with each other in the width direction of the seat.

14. A device, comprising:

a seat comprising a seatback; and a bioinformation measurement device for measuring a bioinformation of a seated person who is seated on the seat, wherein the bioinformation measurement device comprises:

- a sensor which outputs an electric signal according to the bioinformation, and comprises a leading wire including a transmission path for the electric signal; and
- a circuit substrate comprising an input terminal connected to the leading wire of the sensor and configured to receive the electric signal from the sensor, and an amplification unit configured to amplify the electric signal input to the input terminal, the sensor and the circuit substrate are disposed in positions adjacent to each other in the seat, a terminal portion of the leading wire extends from a portion of the sensor adjacent to the circuit substrate and is connected to the input terminal in a state abutting the input terminal, and the circuit substrate is attached to the seatback to be positioned at a center of the seatback in a width direction of the seat.

15. The device according to claim 14, wherein the bioinformation measurement device further comprises a plural number of the sensor, the plural number of the sensor are arranged across a gap in the width direction of the seat, and the circuit substrate is disposed within the gap in a state sandwiched between the sensors.

16. The device according to claim 14, wherein the seat further comprises a seat cushion, the sensor and the circuit substrate are attached to each of the seat cushion and the seatback, and a range where the circuit substrate attached to the seat cushion is present in the width direction of the seat, and a range where the circuit substrate attached to the seatback is present in the width direction of the seat, overlap with each other in the width direction of the seat.

* * * * *